(12) United States Patent
Rizvi

(10) Patent No.: US 8,690,892 B2
(45) Date of Patent: Apr. 8, 2014

(54) POSTPARTUM UTERINE MANIPULATORS AND METHODS OF USE THEREOF

(76) Inventor: Syed Rizvi, Hemet, CA (US)

( * ) Notice: Subject to any disclaimer, the term of this patent is extended or adjusted under 35 U.S.C. 154(b) by 1116 days.

(21) Appl. No.: 11/891,717

(22) Filed: Aug. 13, 2007

(65) Prior Publication Data

US 2008/0058833 A1    Mar. 6, 2008

Related U.S. Application Data

(60) Provisional application No. 60/840,918, filed on Aug. 30, 2006.

(51) Int. Cl.
*A61B 17/42* (2006.01)

(52) U.S. Cl.
USPC .......................................................... 606/119

(58) Field of Classification Search
USPC .......... 604/104–109; 606/119, 135–137, 193, 606/205–208, 191
See application file for complete search history.

(56) References Cited

U.S. PATENT DOCUMENTS

| | | |
|---|---|---|
| 3,948,270 A | 4/1976 | Hasson |
| 4,000,743 A | 1/1977 | Weaver |
| 4,038,978 A | 8/1977 | Morris |
| 4,085,756 A * | 4/1978 | Weaver ........................ 606/45 |
| 4,117,839 A | 10/1978 | Morris |
| 4,198,981 A | 4/1980 | Sinnreich |
| 4,430,076 A | 2/1984 | Harris |
| 4,559,944 A | 12/1985 | Jaeger |
| 4,775,362 A | 10/1988 | Kronner |
| 4,976,717 A | 12/1990 | Boyle |
| 5,217,466 A | 6/1993 | Hasson |
| 5,237,985 A | 8/1993 | Hodgson |
| 5,248,304 A * | 9/1993 | Vigdorchik et al. .......... 604/278 |
| 5,351,679 A * | 10/1994 | Mayzels et al. ............... 600/214 |
| 5,368,598 A | 11/1994 | Hasson |
| 5,382,252 A | 1/1995 | Failla |
| 5,409,496 A | 4/1995 | Rowden |
| 5,431,662 A | 7/1995 | Nicholas |
| 5,464,409 A | 11/1995 | Mohajer |
| 5,487,377 A | 1/1996 | Smith et al. |
| 5,540,700 A | 7/1996 | Rowden |
| 5,556,401 A | 9/1996 | Caillouette |
| 5,571,115 A | 11/1996 | Nicholas |
| 5,643,311 A | 7/1997 | Smith |
| 5,645,561 A | 7/1997 | Smith |
| 5,662,676 A | 9/1997 | Koninckx |
| 5,746,750 A | 5/1998 | Prestel |
| 5,840,077 A | 11/1998 | Rowden |
| 5,935,137 A | 8/1999 | Saadat |
| 5,993,461 A | 11/1999 | Abae |
| 6,024,743 A | 2/2000 | Edwards |
| 6,042,590 A | 3/2000 | Sporri |
| 6,066,132 A | 5/2000 | Chen |
| 6,395,012 B1 | 5/2002 | Yoon |
| 6,565,557 B1 | 5/2003 | Sporri |

(Continued)

*Primary Examiner* — Ashley Fishback

(57) ABSTRACT

The present invention relates to postpartum uterine manipulators and methods of use thereof. According to certain embodiments of the invention, the devices generally comprise (a) a primary shaft having a proximal end and a distal end, and which encapsulates an interior shaft; (b) a handle located at the proximal end of the primary shaft, which comprises a ratchet, two fixed rings and a movable thumb piece coupled to the interior shaft; and (c) a tip located at the distal end of the primary shaft, which comprises multiple sections connected by joints that forms a triangular configuration when in an open position.

6 Claims, 18 Drawing Sheets

(56) References Cited

U.S. PATENT DOCUMENTS

| | | |
|---|---|---|
| 6,673,071 B2 | 1/2004 | VanDusseldorp |
| 6,676,680 B1 | 1/2004 | Packer |
| 2005/0137527 A1* | 6/2005 | Kunin ........................ 604/104 |

\* cited by examiner

POSTPARTUM UTERINE MANIPULATORS AND METHODS OF USE THEREOF

CROSS-REFERENCE TO RELATED APPLICATIONS

This patent application claims priority to, and incorporates by reference, U.S. provisional patent application Ser. No. 60/840,918, filed Aug. 30, 2006.

FIELD OF THE INVENTION

The present invention relates to the field of surgical devices and methods of use thereof. More particularly, the present invention relates to surgical devices and methods of use thereof, which allow the manipulation of a postpartum uterus during surgical procedures.

BACKGROUND OF THE INVENTION

Postpartum tubal sterilization is a permanent method of birth control in which a portion of the fallopian tube is interrupted and either tied, cut, clipped, blocked, cauterized or removed after birth. Tubal sterilization is the most commonly used method of birth control, and provides a highly effective method for women choosing to permanently terminate their reproductive ability.

The anatomy of a postpartum uterus is different than the uterus before pregnancy. The uterus undergoes significant anatomical and physiological changes to support a pregnancy. Such changes have been shown to cause a postpartum uterus to become bulkier, heavier, wider and longer. Consequently, traditional surgical devices are not able to adequately perform certain procedures that a postpartum woman may desire, such as tubal sterilization, insofar as such devices are not designed to accommodate the above-mentioned anatomical changes in the uterus.

Indeed, while several devices for uterine manipulation have been described in the prior art, such devices are not adequate for use on a postpartum uterus. In many cases, the prior art devices were designed for use on a pre-pregnant uterus and, therefore, are not able to effectively accommodate the postpartum anatomical changes described above. Accordingly, a need exists for surgical devices that may be used to manipulate a postpartum uterus during a surgical procedure, including without limitation during a tubal sterilization procedure.

SUMMARY OF THE INVENTION

According to certain embodiments of the invention, surgical devices are provided that may be used to manipulate and maneuver a postpartum uterus. Such devices generally comprise (a) a primary shaft having a proximal end and a distal end, which encapsulates a second interior shaft; (b) a handle located at the proximal end of the primary shaft, which comprises a ratchet, two fixed rings and a movable thumb piece coupled to the interior shaft; and (c) a tip located at the distal end of the primary shaft, which comprises multiple sections connected by joints that form a triangular configuration when in an open position. The open triangular configuration is appropriately dimensioned to be complementary to and accommodate the dimensions of a postpartum uterus.

According to additional embodiments of the present invention, methods for manipulating a postpartum uterus of a patient are provided. Such methods generally comprise (a) placing the patient in a dorsolithotomy position; (b) inserting the primary shaft of the device described above (and described in more detail below) in the uterus of the patient, wherein the tip is in a closed (linear) position; (c) pushing the movable thumb piece forward, thereby causing the tip to open and form a triangular configuration; and (d) manipulating the uterus of the patient by (i) grasping the handle of the device using the two fixed rings and (ii) pulling, pushing, lifting, or maneuvering the uterus by applying force thereto using the device.

According to further embodiments of the present invention, methods for postpartum tubal sterilization are provided. Such methods generally comprise (a) placing the patient in a dorsolithotomy position; (b) inserting the primary shaft of the device described above (and described in more detail below) in the uterus of the patient, wherein the tip is in a closed position; (c) pushing the movable thumb piece forward, thereby causing the tip to open and form a triangular configuration, and engaging the ratchet to lock the movable thumb piece in a forward position; (d) making a transverse, infraumbilical skin incision, which is carried down through a layer of underlying fascia until a layer of peritoneum is identified and entered; (e) lifting the uterus to a position closer to the incision by (i) grasping the handle of the device using the two fixed rings and (ii) lifting the uterus to a location that is adjacent to an anterior abdominal wall of the patient; (f) moving the uterus to the left or right to identify a first fallopian tube; (g) grasping the first fallopian tube using a clamp, following the first fallopian tube out to a first fimbria and ligating and excising a first segment of the first fallopian tube; (h) grasping a second fallopian tube using a clamp, following the second fallopian tube out to a second fimbria and ligating and excising a segment of the second fallopian tube; (i) closing the peritoneum, fascia and the skin of the patient; (j) disengaging the ratchet, thereby causing the thumb piece to release backwards and close the tip; and (k) removing the device from the uterus.

According to yet further embodiments of the present invention, methods for uterine tamponade for treating patients suffering from uterine hemorrhage are provided. Such methods generally comprise (a) placing a patient in a dorsolithotomy position; (b) inserting the primary shaft of the device described herein in the uterus of the patient, wherein the tip is in a closed position and is surrounded by a double-walled inflatable sheath; (c) pushing the movable thumb piece forward, thereby causing the tip to open and form a triangular configuration, and engaging the ratchet to lock the movable thumb piece in a forward position; (d) inflating the sheath with air or fluid; and (e) applying pressure on a wall of the uterus to control the hemorrhage.

According to still further embodiments, the present invention provides (1) a device to reduce the risk of complications associated with postpartum tubal sterilization (and for reducing the operating time that is typically required for such procedures), (2) a method to reduce the complexity of postpartum tubal sterilization in high-risk patients, such as obese patients or patients with pelvic and abdominal adhesions, (3) a device and method for uterine stabilization during postpartum tubal sterilization procedures, (4) a method for providing a surgeon with maximum control during a postpartum tubal sterilization procedure, (5) a device having a tip conforming to the natural shape of the uterine cavity for maximum torque aiding in postpartum uterine manipulation, and (6) a uterine manipulator with a tip that prevents accidental slippage during surgical procedures and provides easy and comfortable removal of the device following surgical procedures.

DETAILED DESCRIPTION OF THE INVENTION

The following will describe in detail several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

According to certain embodiments of the invention, surgical devices are provided that may be used to manipulate and maneuver a postpartum uterus. Such devices generally comprise a primary shaft having a proximal end and a distal end, which encapsulates a second interior shaft. The devices further include a handle located at the proximal end of the primary shaft, which comprises a ratchet, two fixed rings and a movable thumb piece coupled to the interior shaft. In addition, the devices comprise a tip located at the distal end of the primary shaft, which includes multiple sections connected by joints that form a triangular configuration when in an open position. The open triangular configuration is appropriately dimensioned to be complementary to and accommodate the dimensions of a postpartum uterus.

Figure 1:
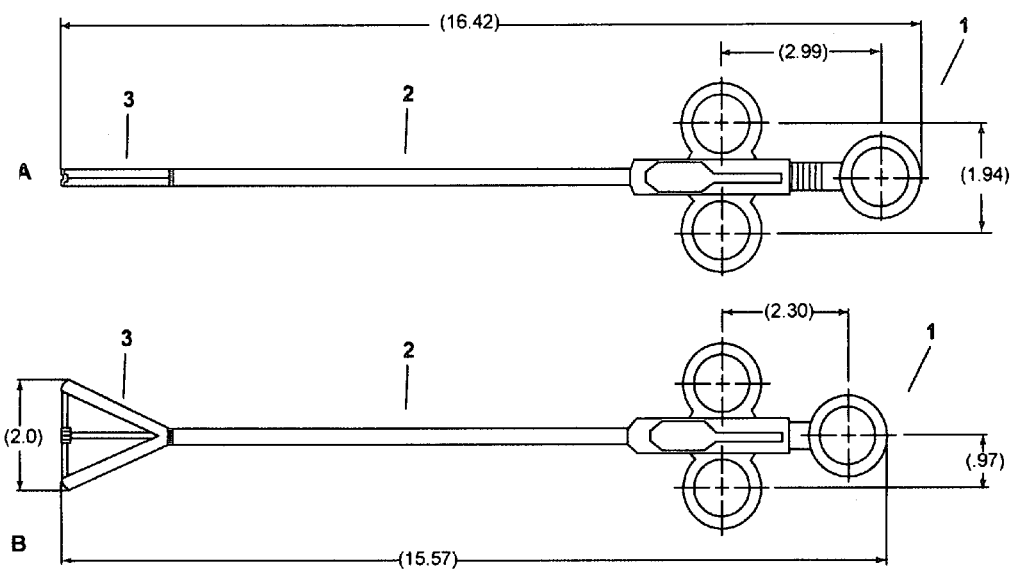
FIG. 1A is a top view of a non-limiting example of a device of the present invention having a closed tip.
FIG. 1B is a top view of a non-limiting example of a device of the present invention having an open tip.
Figure 2:
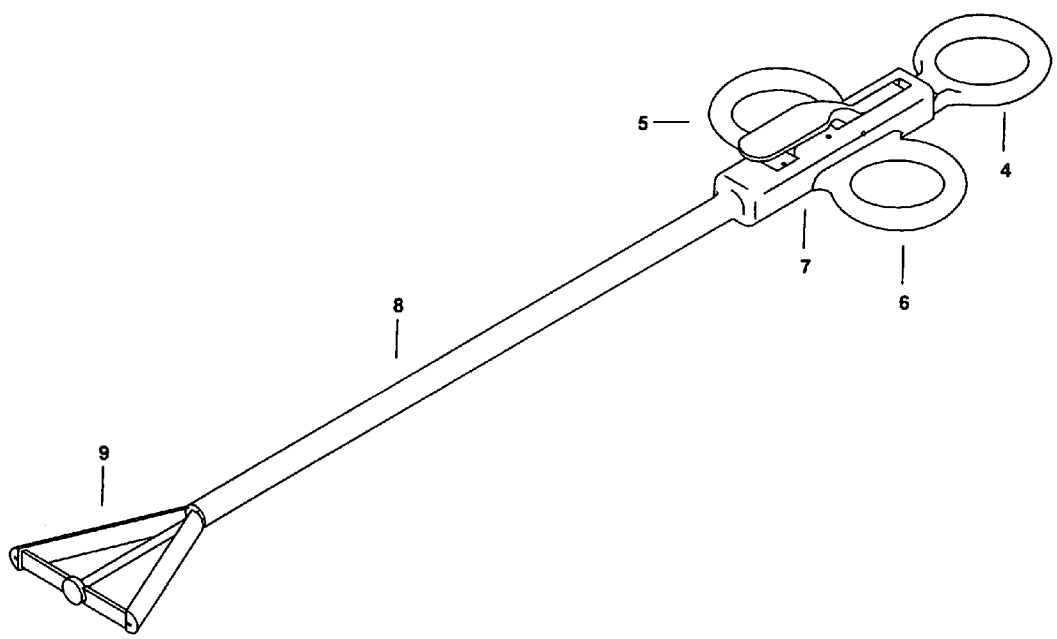
FIG. 2 is a perspective view of a non-limiting example of a device of the present invention having an open tip.
Figure 3:
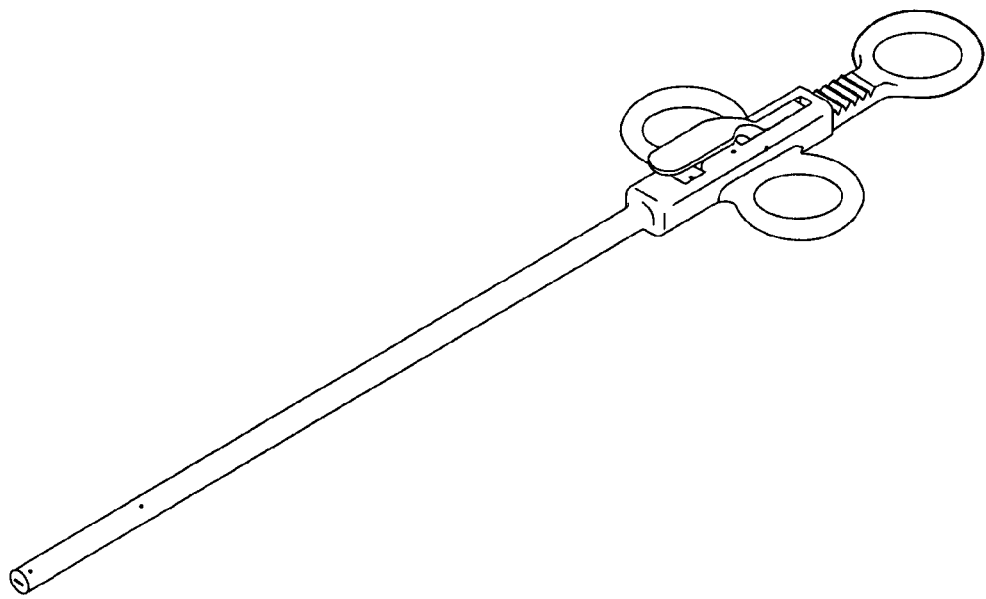
FIG. 3 is a perspective view of a non-limiting example of a device of the present invention having a closed tip.
Figure 4:
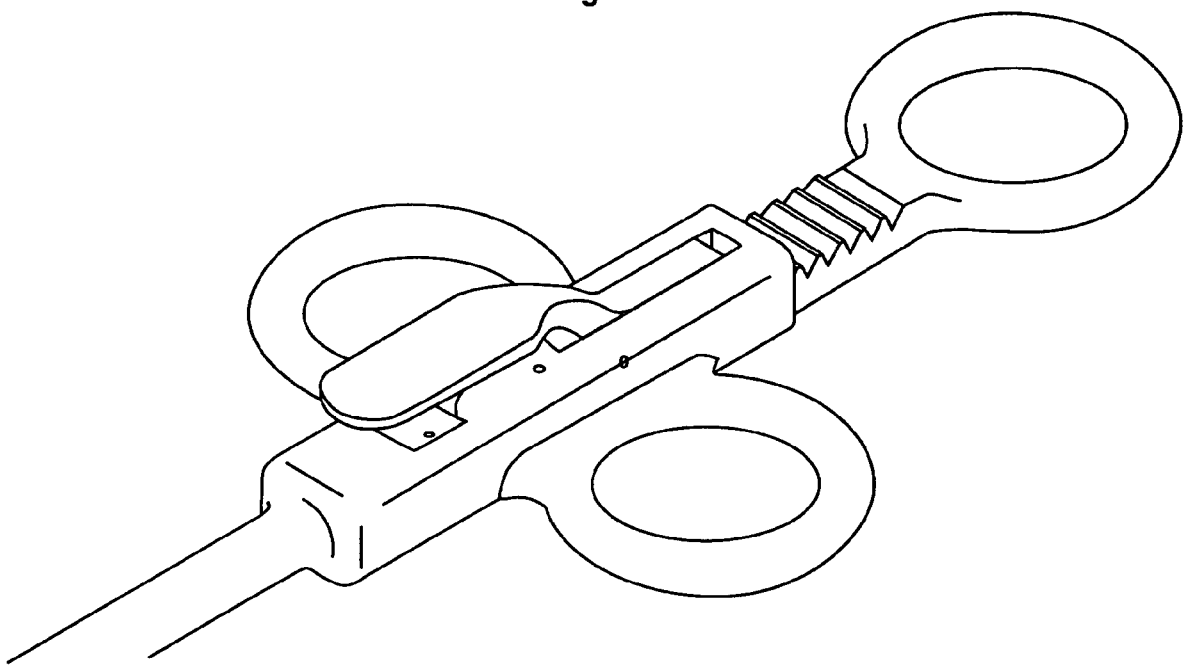
FIG. 4 is a perspective view of the handle of the device of FIGS. 1-3, in which the tip is in a closed position.
Figure 5:
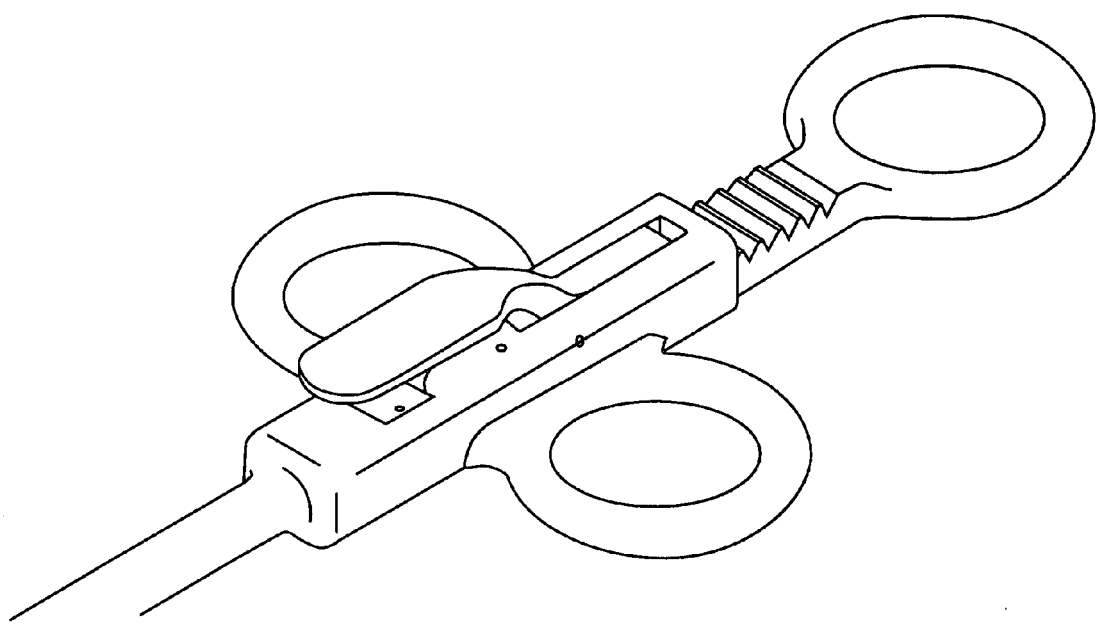
FIG. 5 is a perspective view of the handle of the device of FIGS. 1-3, in which the tip is in an open position.
Figure 6:
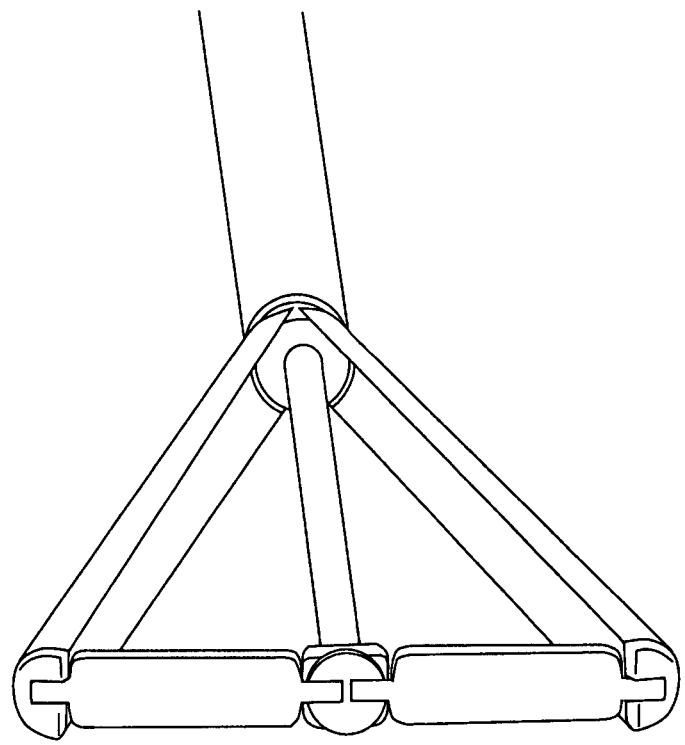
FIG. 6 is a front view of the tip portion of the device of FIGS. 1-3, in which the tip is in an open position.
Figure 7:
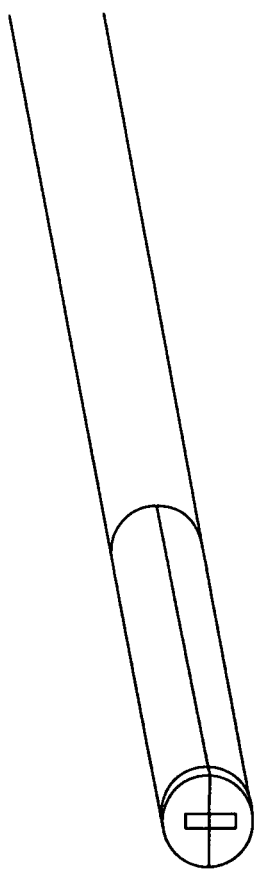
FIG. 7 is a front view of the tip portion of the device of FIGS. 1-3, in which the tip is in a closed position.
Figure 18:
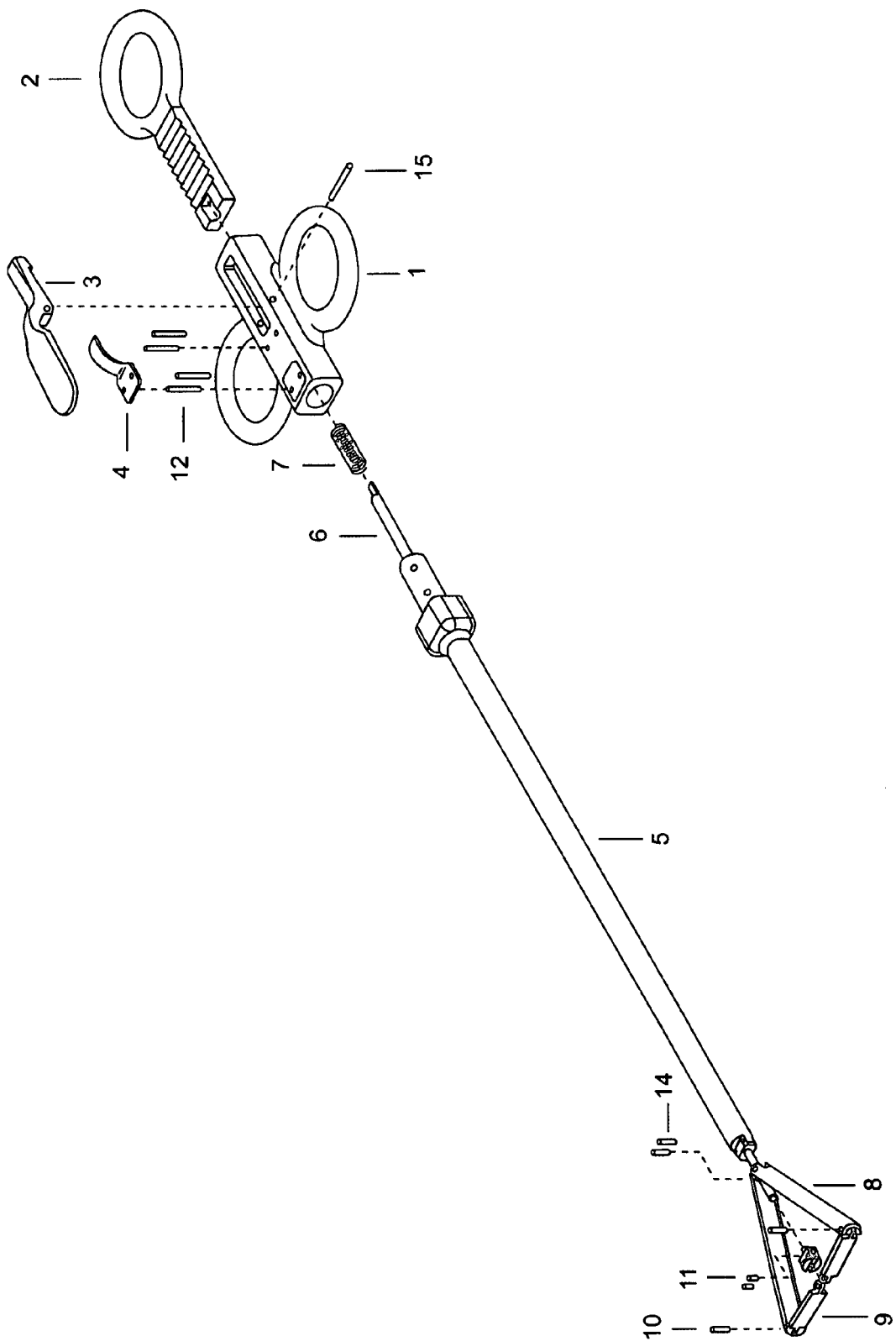
FIG. 18 is a diagram showing the surgical device described herein, in which the components thereof are unassembled.

More specifically, and referring to FIG. 1, the devices of the present invention generally comprise a handle 1, a primary shaft 2, and a tip 3. FIG. 1A shows the tip 3 in a closed position, whereas FIG. 1B shows the tip 3 in an open position. More particularly, referring to FIG. 2, the handle comprises a ratchet 7, two fixed rings 5, 6 and a movable thumb piece 4 coupled to the interior shaft 8 (not shown), wherein pushing the movable thumb piece 4 forward causes the tip 9 to open (as shown in FIG. 2). The handle, including the ratchet, movable thumb piece and fixed rings thereof, are comprised of further parts and components. Referring to FIG. 18, for example, the handle 1 that is shown therein comprises a pull, push and slide rack 2 (which also represents the movable thumb piece described herein), a thumb lock 3, a thumb lock spring 4, an outer housing 5 (also referred to herein as the primary shaft, such as the primary shaft 2 shown in FIG. 1), an interior shaft 6, a compression spring 7, a shaft shroud 8 (also referred to herein as a section of the device tip), an open/close link 9 (which also constitutes a section of the device tip), gate pins 10, interior shaft pins 11, lock pins 12, gate link pins 14, and a thumb lock pin 15.

Figure 19:
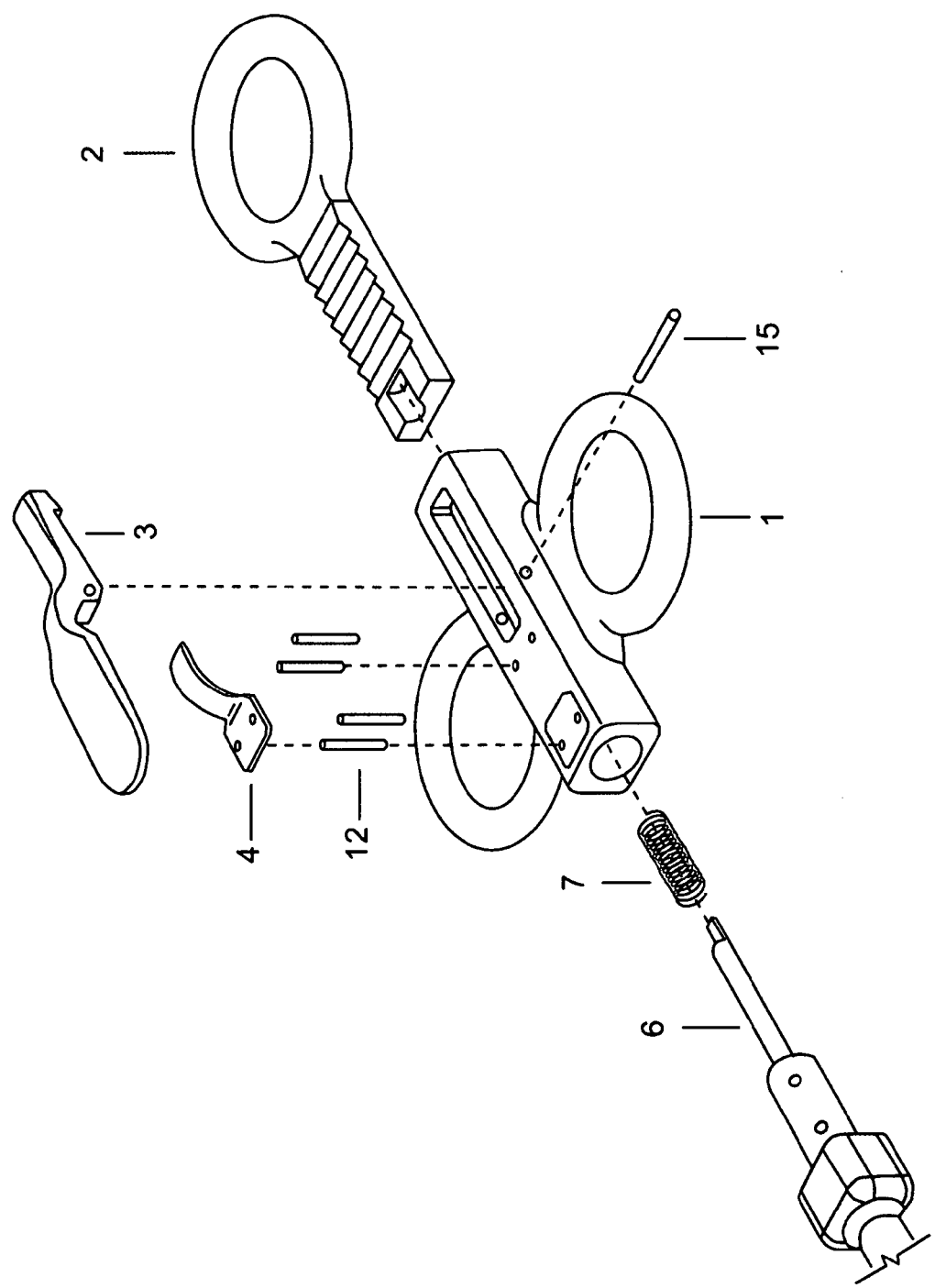
FIG. 19 is a diagram showing the handle of the surgical device described herein, in which the components of the handle are unassembled.

Referring to FIG. 19, which shows an enlarged drawing of the device handle 1, the pull, push and slide rack 2 comprises a series of ridges, which correspondingly mate with the bottom side of the thumb lock 3. When the top side of the thumb lock 3 is pressed from the top surface thereof, the bottom side of the thumb lock 3 disengages the series of ridges of the pull, push and slide rack 2, thereby allowing the pull, push and slide rack 2 (also referred to herein as the movable thumb piece) to be pushed forwards. Referring to FIG. 19, the pull, push and slide rack 2 (movable thumb piece) may be locked into a desired position by releasing (or removing pressure from) the top side of the thumb lock 3, which cause the bottom surface thereof to engage the series of ridges of the pull, push and slide rack 2 in the desired location within such series of ridges. The thumb lock pin 15 secures the thumb lock 3 to the handle and, furthermore, serves as the pivoting axis of the thumb lock 3. The thumb lock spring 4 is secured to the handle by the lock pins 12. The thumb lock spring 4 exerts pressure on the bottom surface of the thumb lock 3, such that the thumb lock 3 engages the series of ridges of the pull, push and slide rack 2 in its non-compressed (or resting) state.

Figure 21:
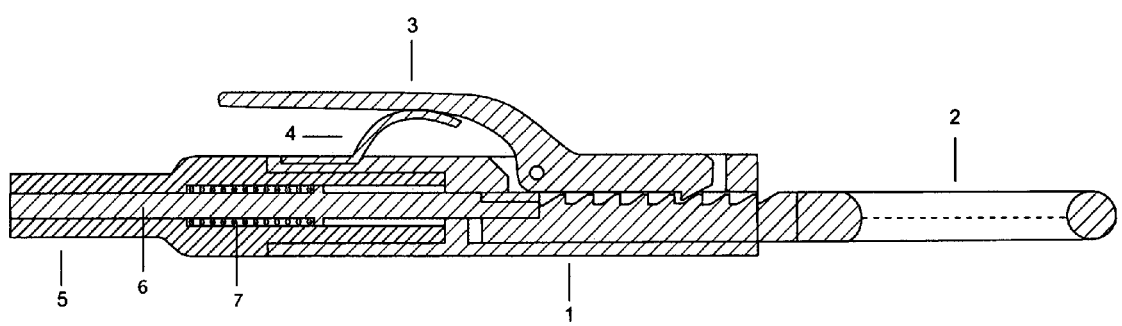
FIG. 21 is a cross-sectional side view of the ratchet portion of the handle of the device described herein.
Figure 22:
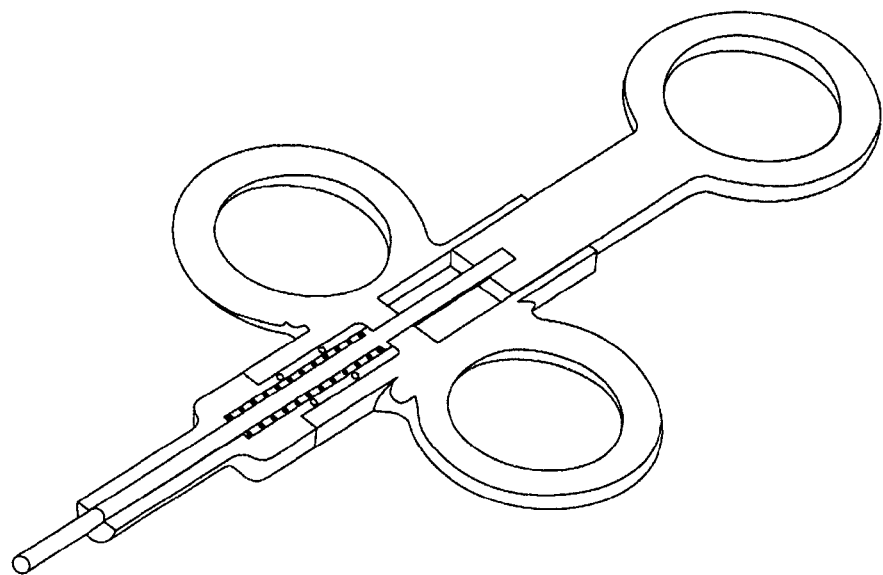
FIG. 22 is a cross-sectional perspective view showing the compression spring of the device handle in closed tip configuration.
Figure 23:
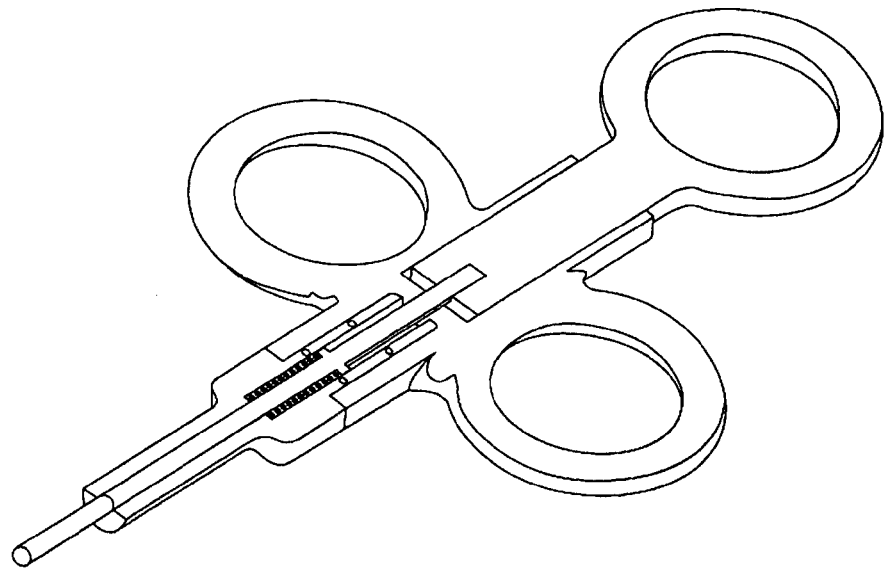
FIG. 23 is a cross-sectional perspective view showing the compression spring of the device handle in open tip configuration.

Still referring to FIG. 19, the interior shaft 6 and compression spring 7 are operably connected to and engage the pull, push and slide rack 2, such that when the pull, push and slide rack 2 is pushed forward, the interior shaft 6 is pushed forward; whereas, when the pull, push and slide rack 2 is pulled backwards, the interior shaft 6 is pulled backwards. More particularly, the compression spring 7 exerts pressure on the interior shaft 6 in such a way that it pushes the pull, push and slide rack 2 backwards. FIG. 21 shows a cross-sectional view of the ratchet portion of the devices described herein. As shown in FIG. 21, the compression spring 7 is disposed within the ratchet such that—in the absence of external forces (e.g., a surgeon's thumb) pushing the pull, push and slide rack 2 forwards—it forces the interior shaft 6 away from the tip (or, in other words, it pushes the pull, push and slide rack 2 backwards). When external forces (e.g., a surgeon's thumb) pushes the pull, push and slide rack 2 forwards, it causes the interior shaft 6 to move forward and the compression spring 7 to compress. Such change in the compression spring 7 is illustrated in FIG. 22 (showing the compression spring 7 in an extended orientation (where the pull, push and slide rack 2 has been pulled backwards creating a closed tip configuration)) and FIG. 23 (showing the compression spring 7 in a compressed orientation (where the pull, push and slide rack 2 has been pushed forwards creating an open tip configuration)).

Figure 20:
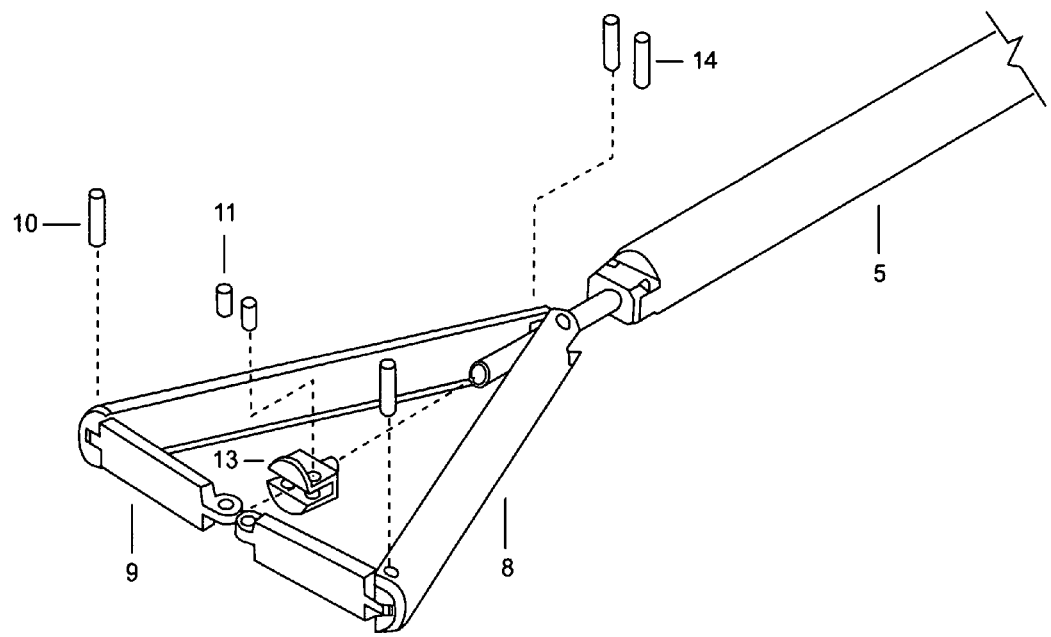
FIG. 20 is a diagram showing the tip portion of the surgical device described herein, in which the components of the tip portion are unassembled.

Referring now to FIG. 20, an enlarged view of the device tip is shown. Specifically, FIG. 20 shows the housing 5 (also referred to herein as the primary shaft, such as the primary shaft 2 shown in FIG. 1), shaft shrouds 8 (also referred to herein as a section of the device tip), an open/close link 9 (which also constitutes a section of the device tip), gate pins 10, interior shaft pins 11, a klevis 13, and gate link pins 14. The gate pins 10 connect and serve as joints (or pivoting axis) between the shaft shrouds 8 and open/close link 9 (the shrouds 8 and open/close link 9 are also collectively referred to herein as the sections of the tip). The gate link pins 14 connect the shrouds 8 at a common point around the interior shaft 6. The klevis 13 is operably connected to the interior shaft 6, such that when the interior shaft 6 is pulled backwards, it causes the open/close link 9 to fold inwards about a joint (or pivoting axis), thereby causing the tip to close. Similarly, klevis 13 is operably connected to the interior shaft 6, such that when the interior shaft 6 is pushed forwards, it causes the open/close link 9 to open (and the two pieces thereof to align), thereby causing the tip to open and exhibit the triangular configuration described herein. The klevis 13 and adjoining portions of the open/close link 9 comprise corresponding through holes in which the interior shaft pins 11 are disposed. The interior shaft pins 11 operate to connect the klevis 13 and adjoining portions of the open/close link 9. The interior shaft pins 11 further operate as the joints (or pivoting axis) about which the open/close link 9 closes when the interior shaft 6 is retracted (pulled backwards). The shrouds 8 may comprise a slight cavity in which the open/close link 9 resides when the interior shaft 6 is retracted (pulled backwards) and the tip closes.

The postpartum uterine manipulators of the present invention may exhibit various dimensions. For purposes of illustration, however, the following provides a non-limiting set of dimensions for a device of the present invention.

| Device Part | Exemplary Dimensions (Inches) |
| --- | --- |
| Handle | 3.50 × 2.50 × 0.50 (L, W, H) |
| Pull, Push Slide Rack | 3.21 × 1.56 × 0.25 (L, W, H) |
| Thumb Lock | 2.52 × 0.50 × 0.56 (L, W, H) |
| Thumb Lock Spring | 0.91 × 0.27 × 0.37 (L, W, H) |
| Primary Shaft (Outer Housing) | 10.29 × 0.50 × 0.62 (L, W, H) |
| Inner Shaft | 12.46 × 0.18 (L, D) |
| Compression Spring | 1.0 × 0.25 (L, D) |
| Shaft Shroud | 2.15 × 0.15 × 0.31 (L, W, H) |
| Open/Close Link | 0.95 × 0.12 × 0.25 (L, W, H) |
| Gate Pin | 0.26 × 0.06 (L, D) |
| Inner Shaft Pin | 0.13 × 0.06 (L, D) |
| Lock Pin | 0.50 × 0.04 (L, D) |
| Klevis | 0.27 × 0.25 × 0.27 (L, W, H) |
| Gate Link Pin | 0.24 × 0.06 (L, D) |
| Thumb Lock Pin | 0.60 × 0.06 (L, D) |

(L, W, H) = Length, Width, Height
(L, D) = Length, Diameter

Figure 17:
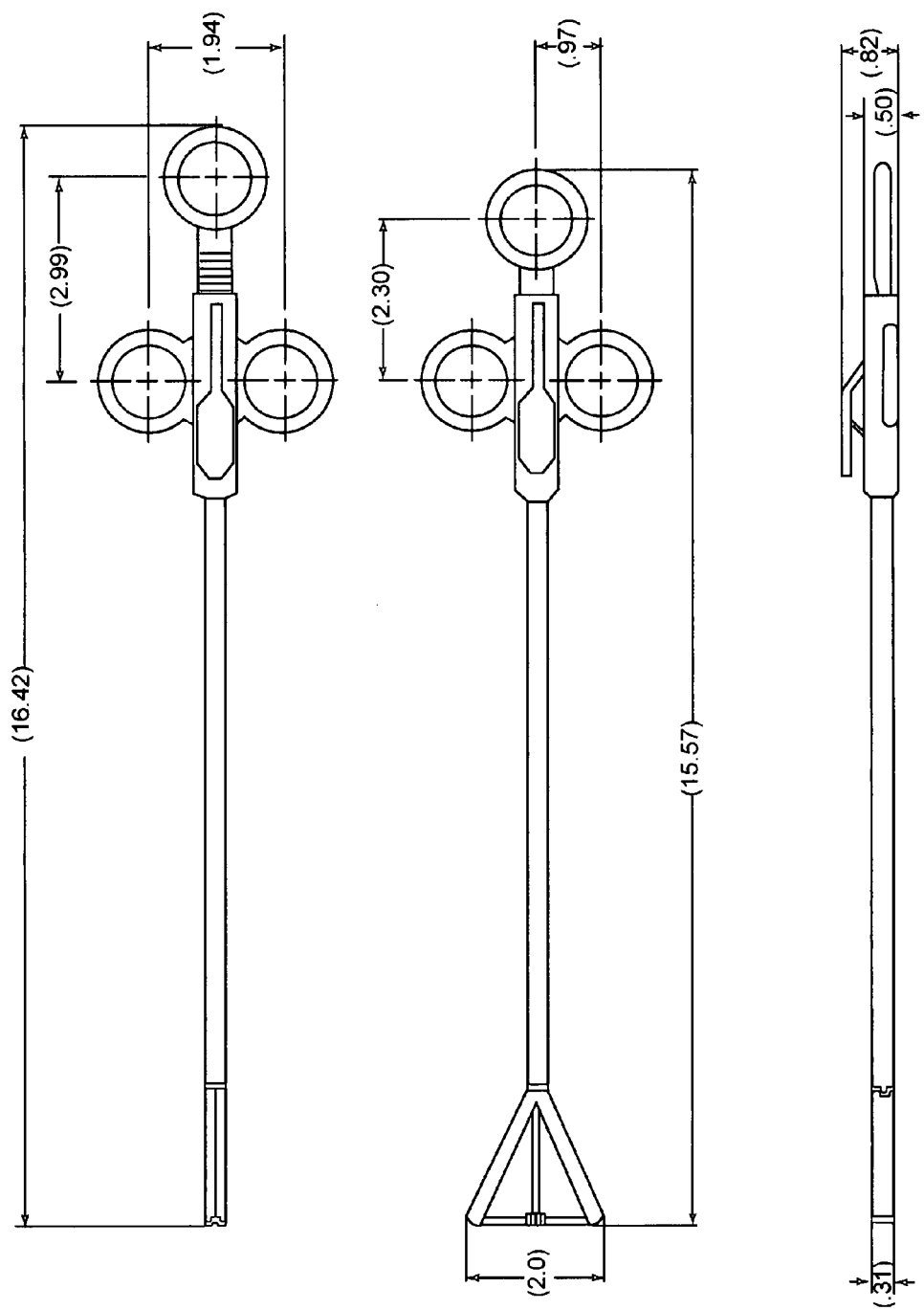
FIG. 17 is a diagram showing the device of FIGS. 1-3, along with non-limiting examples of certain preferred dimensions thereof.

Devices of the foregoing dimensions have been shown to be particularly useful for manipulating and maneuvering the heavier and larger postpartum uterus. Further exemplary dimensions are shown in FIG. 17. In particular, when the tip portion of the device ranges between from about 1.5 inches to about 2.5 inches in length (i.e., the total combined length of both parts of the open/close link 9 when in an open and linear orientation), the device and tip portion thereof is particularly suitable for manipulating and maneuvering a heavier and bulkier postpartum uterus. In certain preferred embodiments, the total combined length of both parts of the open/close link 9 is about 2.0 inches, which has been shown to be particularly suitable for the postpartum uterus of most women.

Figure 15A:
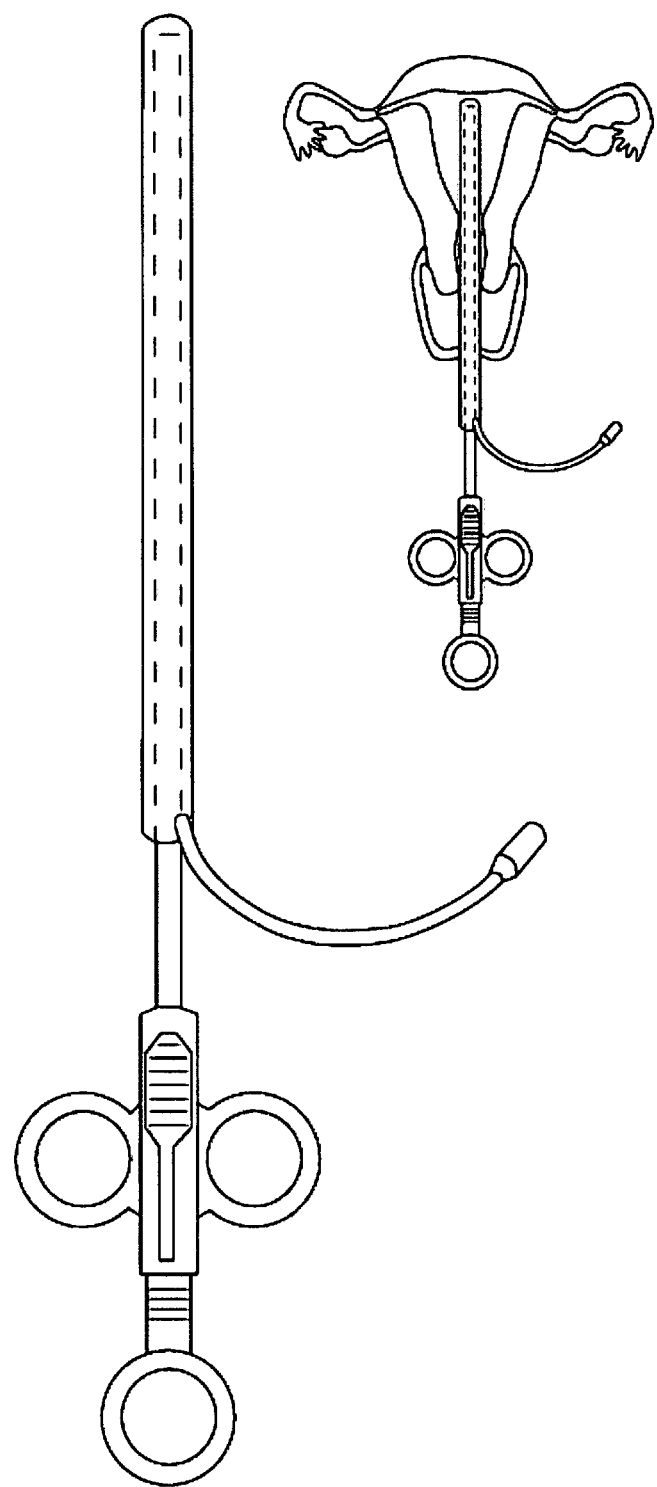
FIGS. 15A, 15B and 15C show the uterine tamponade described herein, which comprises a double-walled inflatable protective sheath encapsulating the tip and primary shaft of the device described herein.
Figure 15B:
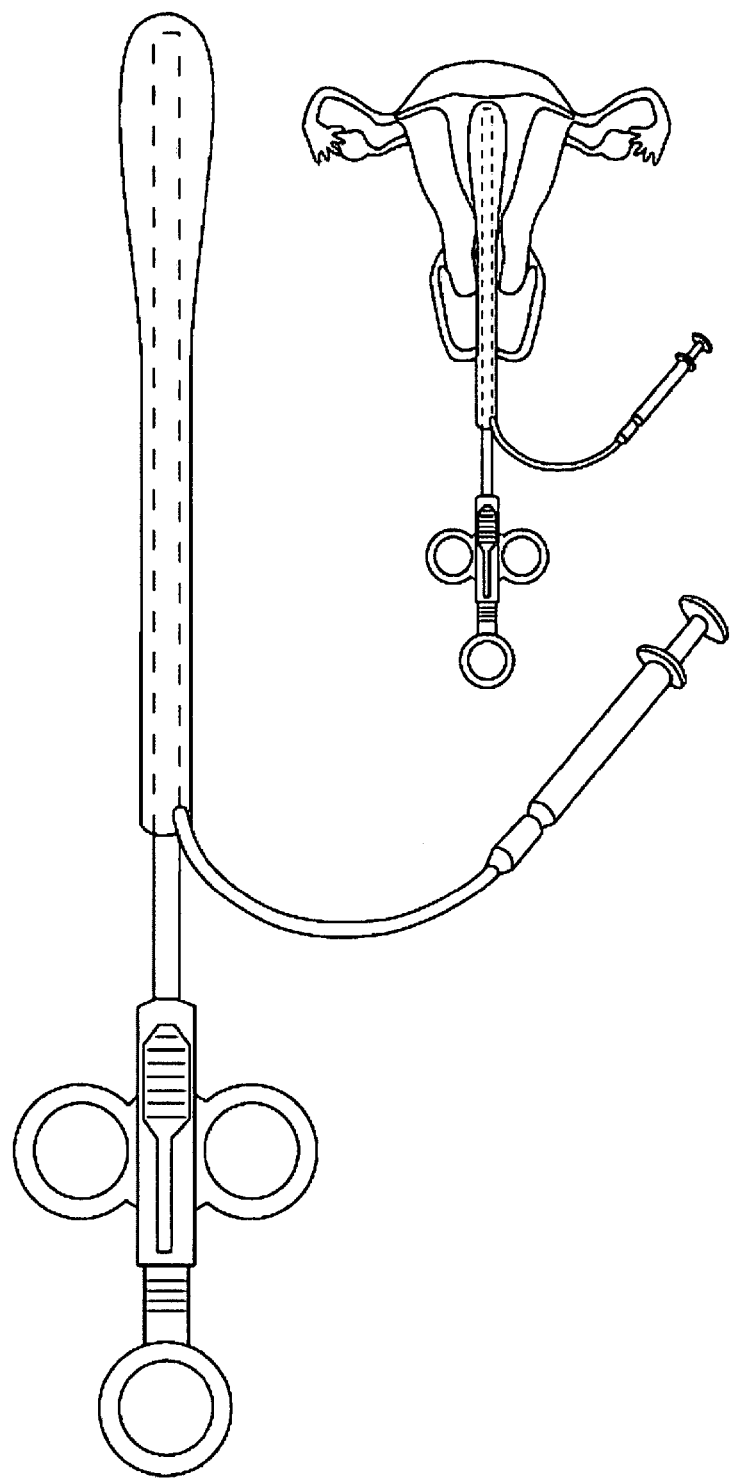
Figure 15C:
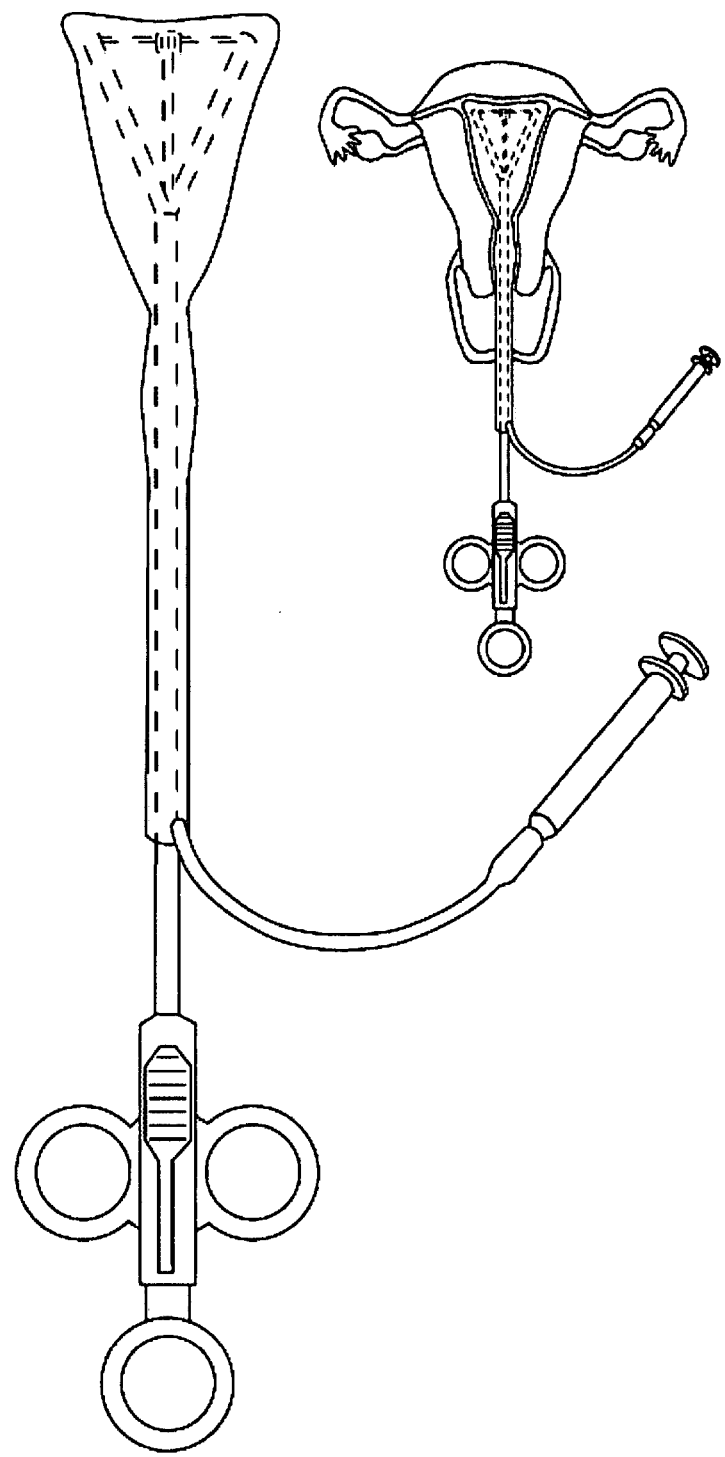
Figure 16:
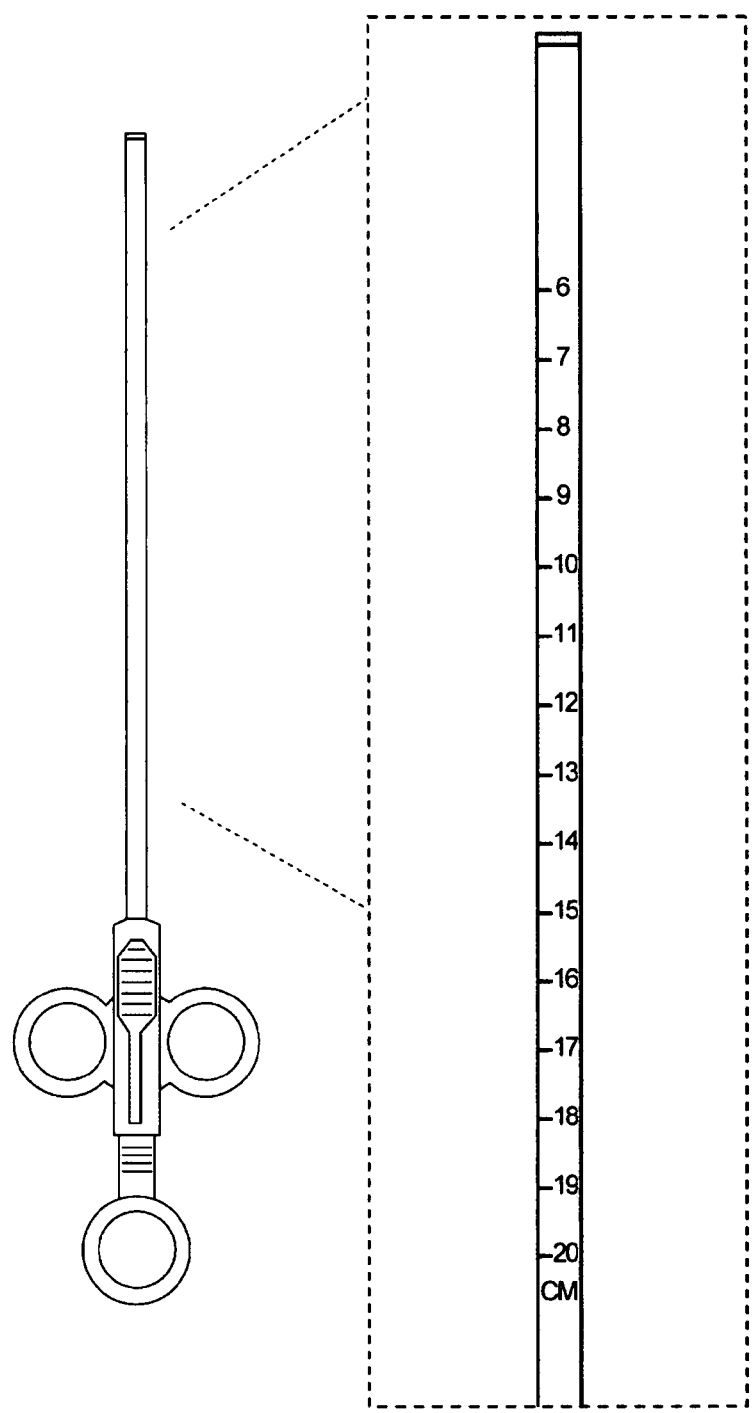
FIG. 16 is a diagram showing the device of FIGS. 1-3, with distance markers on the primary shaft portion thereof.

The postpartum uterine manipulators of the present invention may further comprise a protective inflatable sheath that is placed over the tip of the device for added protection, as the device is advanced into and applied against the walls of the uterus. A non-limiting example of such an inflatable sheath is shown in FIGS. 15A-C. The sheath may comprise a double-walled air-tight material that may be inflated by providing the interior portion thereof with air, gas, or fluid, such as by injecting such air, gas, or fluid through a septum and into the interior portion of the sheath. The postpartum uterine manipulators may further comprise a rubber or plastic cover on the tip portion thereof, which can provide extra protection and padding for the uterine cavity. Still further, referring to FIG. 16, the manipulators may exhibit distance markings on the primary shaft, which can be used to measure the length of the uterine cavity (and the depth of insertion of the device). The postpartum uterine manipulators of the present invention may be disposable or non-disposable, and made of plastic, steel or any other suitable material.

According to additional embodiments of the present invention, methods for manipulating a postpartum uterus of a patient are provided. Such methods generally comprise inserting the primary shaft of the uterine manipulator device described above into the uterus of the patient. The tip of the device is in a closed (linear) position when it is inserted into the patient's uterus. Once inserted into the uterus, the movable thumb piece (the pull, push and slide rack 2 of FIG. 19) is pushed forward, thereby causing the tip to open and form the triangular configuration (or, in other words, causing the interior shaft 6 to move forwards and the open/close link 9 to open and exhibit a linear orientation). Prior to insertion of the device into the uterus, the inflatable sheath described herein (and shown in FIGS. 15A-C) may optionally be provided to the tip and primary shaft of the device, and then inflated after insertion into the uterus. Next, the uterus may be manipulated and maneuvered by (i) grasping the handle of the device using the two fixed rings and (ii) pulling, pushing, lifting, or maneuvering the uterus by applying force thereto using the device.

After the uterus has been manipulated as desired (and the surgical procedure has been performed), the device is removed from the uterus by pulling the movable thumb piece backwards, causing the tip to close, such that is may be easily removed. More particularly, referring to FIG. 19, the top side of the thumb lock 3 is pressed from the top surface thereof, causing the bottom side of the thumb lock 3 to disengage the series of ridges of the pull, push and slide rack 2, thereby allowing the pull, push and slide rack 2 (i.e. the movable thumb piece) to be pulled backwards (through the pressure of the compression spring 7 and/or through the surgeon's own pulling force).

According to further embodiments of the present invention, methods for postpartum tubal sterilization are provided. Such methods generally comprise placing a patient in a dorsolithotomy position after anesthesia is administered. The patient is prepared and draped in a sterile fashion. A vaginal retractor is employed according to well-known procedures and an anterior portion of the cervix may be grasped, if necessary, with a single tooth tenaculum. Furthermore, a uterine sound may be used to evaluate the uterine cavity.

Figure 8:
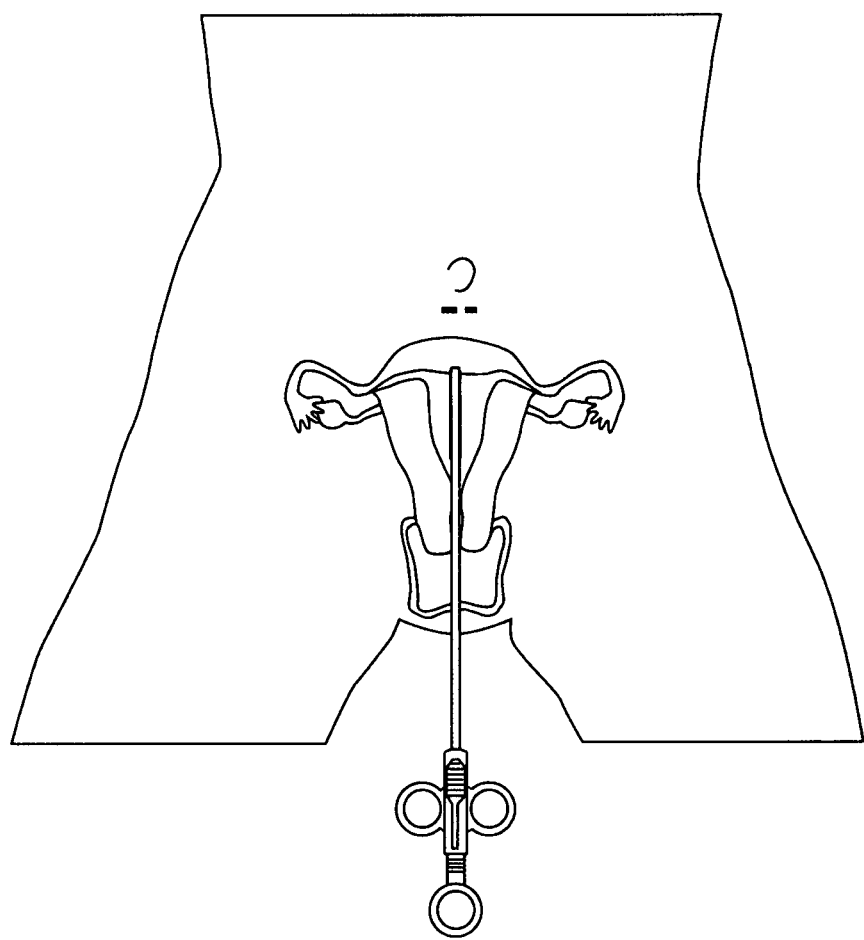
FIG. 8 is a diagram showing the device of FIGS. 1-3 inserted into and positioned within the uterus of a patient, in which the tip of the device is in a closed position.
Figure 9:
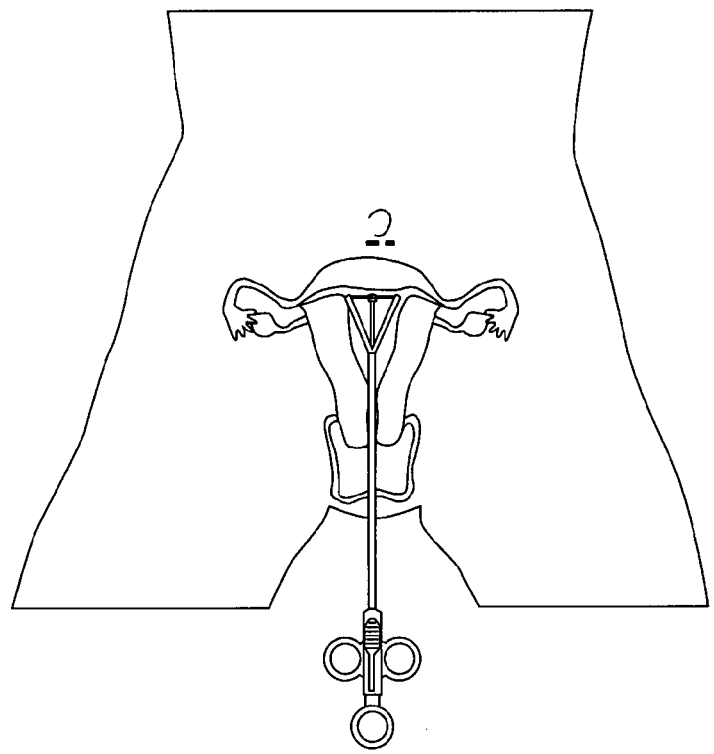
FIG. 9 is a diagram showing the device of FIGS. 1-3 inserted into and positioned within the uterus of a patient, in which the tip of the device is in an open position.
Figure 10:
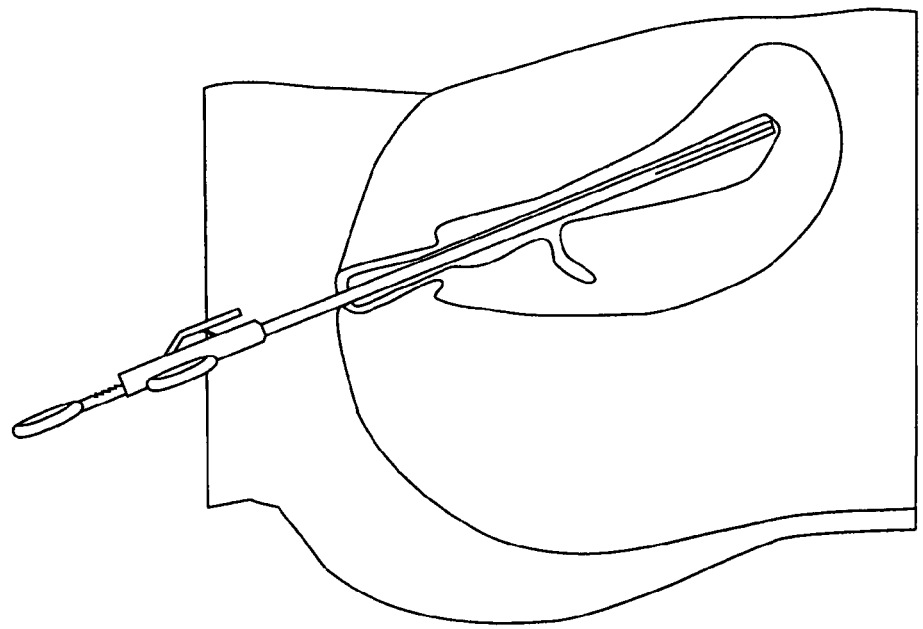
FIG. 10 is a sagittal view of the uterus shown in FIG. 8.

Next, the primary shaft of the device described above in inserted into the uterus of the patient. As shown in FIG. 8, the tip of the device is in a closed position when it is inserted into the uterus. Next, as shown in FIG. 9, the tip of the device is opened, following the procedures outlined above. Prior to insertion of the device into the uterus, the inflatable sheath described herein (and shown in FIGS. 15A-C) may optionally be provided to the tip and primary shaft of the device, and then inflated after insertion into the uterus. A small transverse, infraumbilical skin incision is then made, which is carried down through a layer of underlying fascia until a layer of peritoneum is identified and entered (shown in FIG. 9). A self-retaining retractor may, optionally, be placed through the abdominal incision for ease of operation.

Using the uterine manipulator (having the tip in an open position and exhibiting the triangular configuration described herein), the uterus is maneuvered and lifted to a position closer to the incision. More particularly, for example, the surgeon may grasp the handle of the device using the two fixed rings and then lift the uterus to a location that is adjacent to an anterior abdominal wall of the patient (next to the incision).

Figure 11:
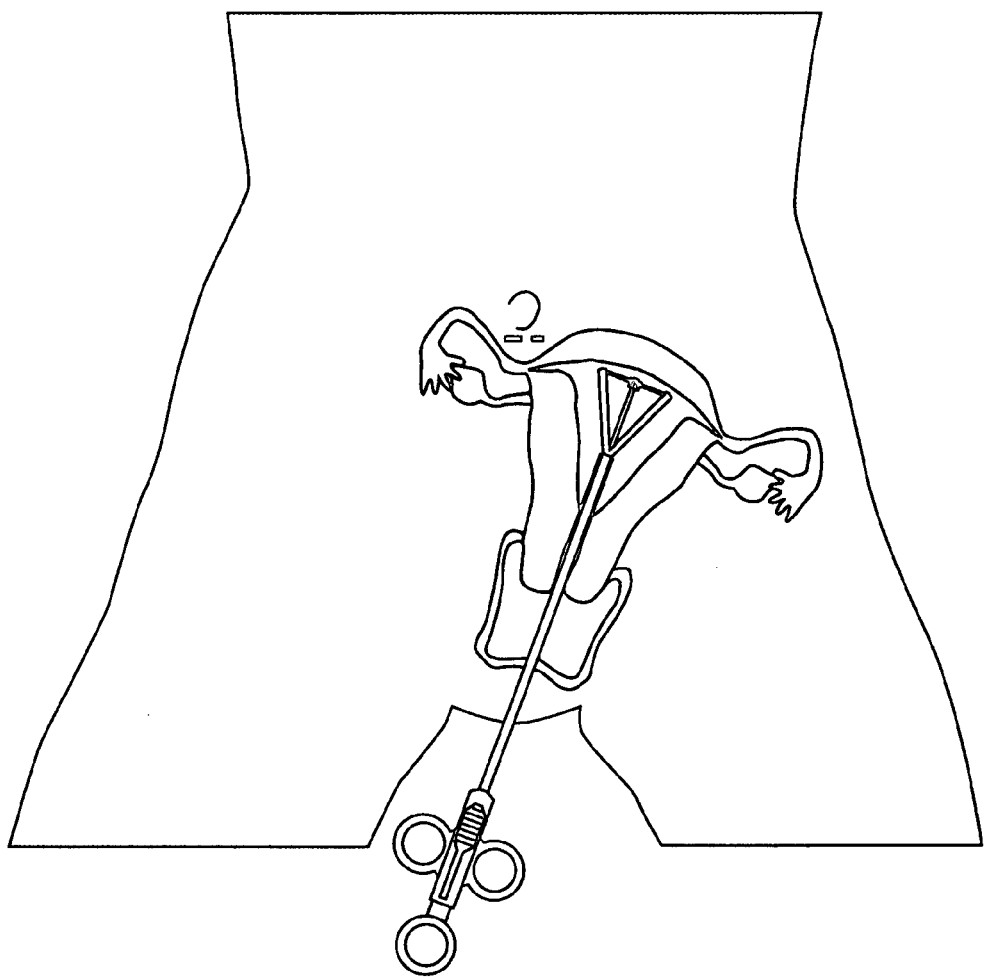
FIG. 11 is a diagram showing the device of FIGS. 1-3 inserted into and positioned within the uterus of a patient, in which the tip of the device is in an open position and is being used to tilt the uterus to the left.
Figure 13:
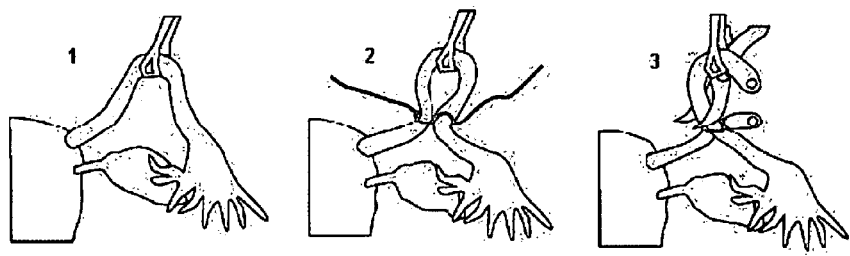
FIG. 13 is a diagram showing a tubal sterilization procedure being carried out on the left fallopian tube, in which the fallopian tube is grasped with a clamp (1), ligated (2) and excised (3).
Figure 14:
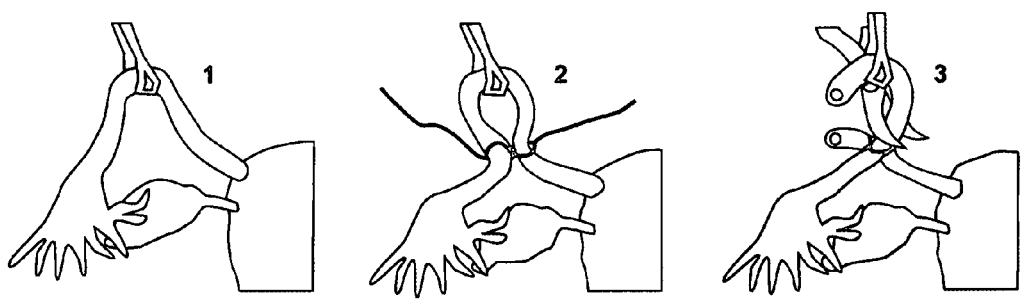
FIG. 14 is a diagram showing a tubal sterilization procedure being carried out on the right fallopian tube, in which the fallopian tube is grasped with a clamp (1), ligated (2) and excised (3).

The uterine manipulator is then used to move the uterus to the left or right to identify a first fallopian tube, as shown in FIG. 11. Once identified, the first fallopian tube is grasped using a clamp and followed until the fimbria is reached. At that point, a segment of the fallopian tube may be ligated and/or excised. Referring to FIGS. 13 and 14, for example, the segments of the left and right fallopian tubes, respectively, are shown to be grasped using a clamp (1), ligated or tied shut (2), and then cut, excised, and removed from the patient (3).

Figure 12:
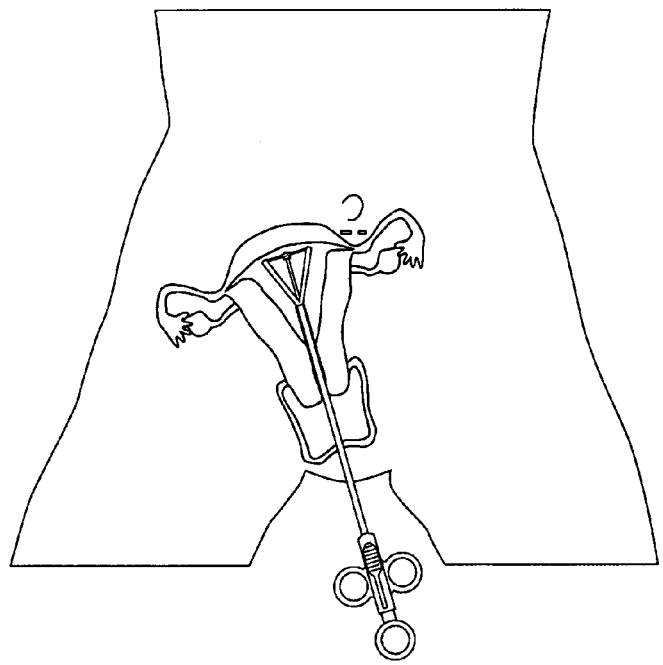
FIG. 12 is a diagram showing the device of FIGS. 1-3 inserted into and positioned within the uterus of a patient, in which the tip of the device is in an open position and is being used to tilt the uterus to the right.

After completing the excision of a first fallopian tube, the uterine manipulator device is used to move the uterus to identify a second (or contralateral) fallopian tube (FIG. 12). Once identified, the second fallopian is clamped, ligated and/or excised as shown in FIGS. 13 and 14. Good homeostasis is assured and the fallopian tube is returned to the abdomen. Next, the peritoneum, fascia and the skin of the patient are closed, the ratchet of the device is disengaged, thereby causing the thumb piece to release backwards and to close the tip, such that the device may be easily and comfortably removed from the uterus.

According to yet further embodiments of the present invention, methods for uterine tamponade for treating patients suffering from uterine hemorrhage are provided. Such methods generally comprise placing a patient in a dorsolithotomy position and inserting the primary shaft of the device described herein into the uterus of the patient. Referring to FIG. 15A, the tip is in a closed position when it is inserted into the uterus and is surrounded by a double-walled inflatable sheath. Next, the movable thumb piece is pushed forward, thereby causing the tip to open and form the triangular configuration described herein. The ratchet of the device is engaged to lock the movable thumb piece in a forward position. Next, referring to FIGS. 15B and 15C, the sheath is inflated with air or fluid. Finally, pressure is applied to the wall(s) of the uterus to control the hemorrhage. Once the hemorrhage has ceased, the device may be removed from the uterus as described herein.

The uterine manipulator devices described herein may be used and employed in a variety of methods and surgical procedures—all of which are encompassed by the present invention. For example, the present invention provides (1) a device to reduce the risk of complications associated with postpartum tubal sterilization (and for reducing the operating time that is typically required for such procedures), (2) a method to reduce the complexity of postpartum tubal sterilization in high-risk patients, such as obese patients or patients with pelvic and abdominal adhesions, (3) a device and method for uterine stabilization during postpartum tubal sterilization procedures, (4) a method for providing the surgeon with maximum control during a postpartum tubal sterilization procedure, (5) a device having a tip conforming to the natural shape of the uterine cavity for maximum torque aiding in postpartum uterine manipulation, (6) a uterine manipulator with a tip that prevents accidental slippage during surgical procedures and provides easy and comfortable removal of the device following surgical procedures, and (7) a device for manipulating a non-postpartum uterus during laparoscopic procedures and other surgeries on a non-postpartum uterus.

The uterine manipulator devices of the present invention provide numerous advantages over the prior art devices. For example, many prior art devices do not provide a durable, ergonomic, and easily maneuverable handle, which has been shown to be critical to the ability to efficiently manipulate a heavier and bulkier postpartum uterus. The handle used in the devices of the present invention allows the heavier and bulkier uterus to be brought to an infraumbilical incision, as described above, with ease so that fallopian tubes may be easily identified, ligated and dissected during a sterilization procedure. The handle allows the uterus to be moved as needed, so that the tubes always remain in the surgeon's field of vision. The three-ring shape of the handle provides for easy manipulation of the device using the thumb, index finger and middle finger, which is ergonomically convenient and an efficient way to manipulate the bulky, heavy postpartum uterus and provides maximum torque. In addition, the ratchet mechanism of the device provides a reliable, fast, easy and efficient way to open and close the tip.

The devices of the present invention allow the uterus to be manipulated anteriorly, posteriorly and side ways using the handle. Such manipulation may be used to bring the fundus close to an anterior abdominal wall, thereby allowing better visualization of the fallopian tube during, for example, sterilization procedures. This also brings the fallopian tube within easy reach of the surgeon through a mini-incision on the abdominal wall. The device also allows tilting of the uterus left and right to better visualize each fallopian tube and to provide optimum access to each tube during surgery.

The device of the present invention has also been shown to provide protection against accidental retraction and/or laceration of fallopian tubes (and the surrounding tissue) by stabilizing the uterus. This device not only makes it easier to perform a surgical procedure, but also decreases the risks of complications. This device has also been shown to decrease the operating time and cost of surgical procedures, such as sterilization procedures.

Postpartum tubal sterilization is difficult to perform under regional anesthesia due to the lack of muscle relaxation and difficulty in localizing the fallopian tubes. The uterine manipulator devices of the present invention allow for easier postpartum tubal sterilization under regional anesthesia. The devices provide enhanced control over the operating site and allow for smaller incisions, thereby causing less bleeding, less postoperative pain and faster recovery.

It is to be understood that both the general description and the detailed description are exemplary and explanatory, but are not restrictive of the invention. The invention in its broader aspects is not limited to the specific details shown and described, and departures may be made from such details without departing from the principles of the invention and without sacrificing its chief advantages.

What is claimed is:

1. A method for postpartum tubal sterilization, which comprises:
   (a) placing a patient in a dorsolithotomy position;
   (b) with a first hand, inserting a primary shaft of a device in a postpartum uterus of the patient, wherein a tip of the primary shaft of the device is in a closed linear position, wherein the device comprises:
      (i) the primary shaft having a proximal end and a distal end, wherein the primary shaft encapsulates an interior shaft;
      (ii) a handle located at the proximal end of the primary shaft, wherein the handle comprises a ratchet, two fixed rings and a movable thumb piece coupled to the interior shaft, wherein the ratchet comprises a series of ridges that correspondingly mate with a bottom side of a thumb lock;
      (iii) the tip located at the distal end of the primary shaft, wherein the tip comprises multiple sections connected by joints and forms a triangular configuration when in an open position; and
      (iv) a compression spring that exerts a constant force on the interior shaft in a direction opposite from the tip;
   (c) with the first hand, pushing the movable thumb piece forward, thereby causing the tip to open and form the triangular configuration, and engaging the ratchet to lock the movable thumb piece in a forward position;
   (d) making a transverse, infraumbilical skin incision, which is carried down through a layer of underlying fascia until a layer of peritoneum is identified and entered;
   (e) with the first hand, lifting the uterus to a position closer to the incision by (i) grasping the handle of the device using the two fixed rings and (ii) lifting the uterus to a location that is adjacent to an anterior abdominal wall of the patient;
   (f) moving the uterus to the left or right to identify a first fallopian tube;
   (g) grasping the first fallopian tube using a clamp, following the first fallopian tube out to a first fimbria and ligating and excising a first segment of the first fallopian tube;
   (h) grasping a second fallopian tube using a clamp, following the second fallopian tube out to a second fimbria and ligating and excising a segment of the second fallopian tube;
   (i) closing the peritoneum, fascia and the skin of the patient;
   (j) disengaging the ratchet with the first hand, thereby causing the thumb piece to release backwards and close the tip into the linear position; and
   (k) removing the device from the uterus.

2. The method of claim 1, wherein a section of the tip most proximal to the handle ranges from about 1.5 inches to about 2.5 inches in length.

3. The method of claim 2, wherein the section of the tip most proximal to the handle is about 2.0 inches in length.

4. The method of claim 3, which further comprises (i) providing the tip of the primary shaft with a double-walled inflatable sheath and (ii) injecting air or fluid into the sheath after the primary shaft is inserted into the uterus and the tip is opened to form the triangular configuration.

5. The method of claim 1, wherein the movable thumb piece is located in proximity to the two fixed rings, such that the movable thumb piece will receive a thumb of the first hand, a first of the two fixed rings will receive an index finger of the first hand, and a second of the two fixed rings will receive a middle finger of the first hand, wherein:
   (i) the thumb piece and two fixed rings exhibit a circular configuration; and
   (ii) a center of the thumb piece is no more than 3 inches from a center of each of the two fixed rings.

6. The method of claim 5, wherein the primary shaft that is inserted into the uterus of the patient comprises a plurality of distance markings.

\* \* \* \* \*